(12) United States Patent
Hunter et al.

(10) Patent No.: US 8,521,270 B2
(45) Date of Patent: Aug. 27, 2013

(54) QUANTITATIVE EEG METHOD TO IDENTIFY INDIVIDUALS AT RISK FOR ADVERSE ANTIDEPRESSANT EFFECTS

(75) Inventors: Aimee M. Hunter, Santa Monica, CA (US); Andrew F. Leuchter, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 882 days.

(21) Appl. No.: 12/303,239

(22) PCT Filed: Jun. 5, 2007

(86) PCT No.: PCT/US2007/070438
§ 371 (c)(1),
(2), (4) Date: Sep. 17, 2009

(87) PCT Pub. No.: WO2007/143663
PCT Pub. Date: Dec. 13, 2007

(65) Prior Publication Data
US 2010/0016751 A1    Jan. 21, 2010

Related U.S. Application Data

(60) Provisional application No. 60/811,369, filed on Jun. 5, 2006.

(51) Int. Cl.
*A61B 5/04* (2006.01)
(52) U.S. Cl.
USPC .......................................... 600/544

(58) Field of Classification Search
USPC .................................. 600/544–545
See application file for complete search history.

(56) References Cited

U.S. PATENT DOCUMENTS

| 2003/0135128 A1 | 7/2003 | Suffin et al. | |
| 2003/0181821 A1* | 9/2003 | Greenwald et al. | 600/544 |
| 2005/0216071 A1 | 9/2005 | Devlin et al. | |
| 2005/0251419 A1 | 11/2005 | Suffin et al. | |
| 2006/0167370 A1* | 7/2006 | Greenwald et al. | 600/544 |

OTHER PUBLICATIONS

Cook et al. (Changes in prefrontal activity characterize clinical response in SSRI nonresponders: a pilot study) Journal of Psychiatric Research 39 (2005) 461-466.*
International Search Report mailed on Dec. 13, 2007, for International Application No. PCT/US07/70438 filed on Jun. 5, 2007, 2 pages.

* cited by examiner

*Primary Examiner* — Patricia Mallari
*Assistant Examiner* — Christian Jang
(74) *Attorney, Agent, or Firm* — Morgan, Lewis & Bockius LLP; Annette S. Parent

(57) ABSTRACT

Methods, apparatus, and systems are provided for efficiently and accurately identifying individuals at risk for adverse effects from psychotropic or CNS-active treatment. Changes in a brain activity indicator (e.g. EEG cordance) are used to predict the adverse effects of treatment based on an experimentally derived cutoff value. For example, a reliable biological indicator is provided with high predictive capability for identifying, very early in the course of treatment (e.g. <=48 hours after start of treatment), those individuals who are at greatest risk for worsening suicidality and other adverse effects of antidepressant drugs.

37 Claims, 14 Drawing Sheets

Healthy Subjects

|  | Medication (n = 17) | Placebo (n = 15) | Fisher's Exact |
|---|---|---|---|
| Depressed mood | 5.9% | 0 |  |
| Anxiety | 52.9% | 26.7% | 0.166 |
| Hostility | 29.4% | 6.7% | 0.178 |
| Suicidal Ideation | 0 | 0 |  |

Depressed Subjects

|  | Medication (n = 37) | Placebo (n = 35) | Fisher's Exact |
|---|---|---|---|
| Depressed mood | 8.11% | 17.14% | 0.301 |
| Anxiety | 37.84% | 40.00% | 1.00 |
| Hostility | 16.22% | 8.57% | 0.480 |
| Suicidal Ideation | 13.51% | 22.86% | 0.367 |

*Fig. 6a*

Placebo Subjects     600

| | Healthy (n = 17) | | Depressed (n = 37) | |
|---|---|---|---|---|
| | Model | coef/se/p | Model | coef/se/p |
| Depressed mood | MRFC48 | N/A | MRFC48 | 0.1960 (0.8408) 0.8115 |
| | Constant | N/A | | -1.4608 (0.4820) |
| Anxiety | MRFC48 | -0.4357 (0.9477) 0.6696 | MRFC48 | 0.1035 (0.6975) 0.8825 |
| | Constant | -0.8822 (0.6368) | | -0.6143 (0.3924) |
| Hostility | MRFC48 | -1.5400 (1.8710) 0.4000 | MRFC48 | 0.2696 (1.3838) 0.8516 |
| | Constant | -2.5016 (1.0959) | | -2.6415 (0.7415) |
| Suicidal Ideation | MRFC48 | N/A | MRFC48 | 0.4029 (0.8411) 0.6345 |
| | Constant | N/A | | -1.5037 (0.4940) |

Fig. 6b

| Medication Subjects | | Healthy (n = 17) | | 650 Depressed (n = 37) | |
|---|---|---|---|---|---|
| | | Model | coef/se/p | Model | coef/se/p |
| Depressed mood | | MRFC48 | -4.8994 (5.0205) 0.2353 | MRFC48 | 2.3015 (1.1909) 0.0265\*\* |
| | | Constant | -9.8824 (9.1981) | | -2.8414 (0.8975) |
| Anxiety | | MRFC48 | -1.2732 (0.8556) 0.1269 | MRFC48 | 0.1623 (0.4530) 0.7292 |
| | | Constant | -0.7255 (0.7476) | | -0.4546 (0.3575) |
| Hostility | | MRFC48 | -1.4961 (0.9088) 0.0902\* | MRFC48 | -0.1641 (0.5928) 0.7826 |
| | | Constant | -2.0999 (1.0199) | | -1.6915 (0.4878) |
| Suicidal Ideation | | MRFC48 | N/A | MRFC48 | -1.7550 (0.8314) 0.0204\*\* |
| | | Constant | N/A | | -2.8783 (0.8632) |

\* uncorrected exact p < 0.1
\*\* uncorrected exact p < 0.05

ROC Curve
Hostility in Healthy Subjects

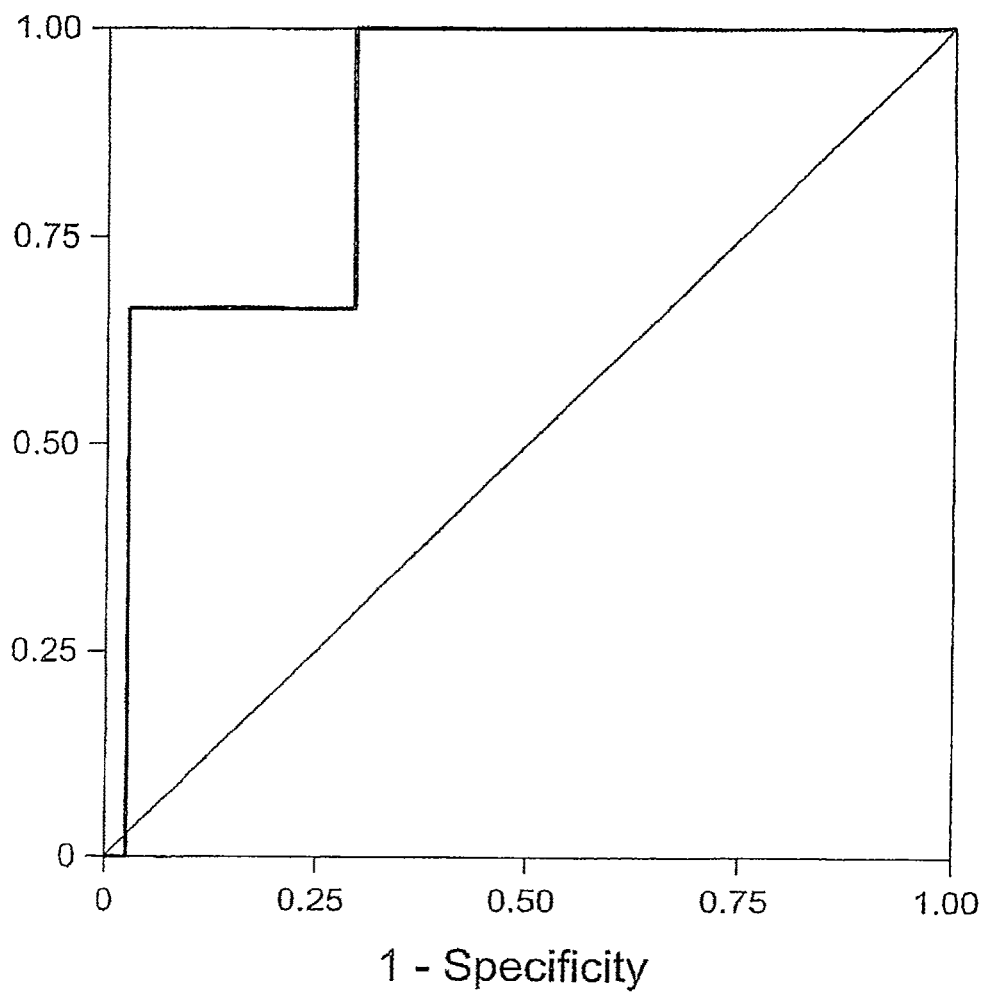

QUANTITATIVE EEG METHOD TO IDENTIFY INDIVIDUALS AT RISK FOR ADVERSE ANTIDEPRESSANT EFFECTS

CROSS-REFERENCES TO RELATED APPLICATIONS

The present application claims priority to U.S. Ser. No. 60/811,369 entitled "QUANTITATIVE EEG METHOD TO IDENTIFY INDIVIDUALS AT RISK FOR ADVERSE ANTIDEPRESSANT EFFECTS", filed Jun. 5, 2006, which is herein incorporated by reference in their entirety.

STATEMENT AS TO RIGHTS TO INVENTIONS MADE UNDER FEDERALLY SPONSORED RESEARCH OR DEVELOPMENT

This invention was made with Government support of Grant No. AT002479 awarded by the National Institutes of Health. The Government has certain rights in this invention.

BACKGROUND

This invention generally relates to the diagnostic testing for identifying individuals at risk for adverse effects from psychotropic or CNS-active treatments, and more particularly to using quantitative electroencephalography (QEEG) to identify individuals at risk for adverse antidepressant effects, such as suicidality.

Major depressive disorder (MDD) is a common illness, associated with high morbidity, mortality, and a very high economic cost for society. Treatment with antidepressant medications is associated with significant improvements of clinical symptoms of depression, as well as improvements of patients' functional status and quality of life. Due to the high prevalence of depression, millions in the U.S. alone are candidates for treatment with antidepressants every year.

Antidepressant medications have demonstrated efficacy for the symptoms of depression and, overall, antidepressant treatment is associated with improved mood and decreased suicidality. However, some individuals may experience worsening mood and suicidality during antidepressant treatment. For example, there is some evidence that antidepressant medications may be associated with increases in suicidal ideation and elevated risk for harm-related adverse events in a small subset of depressed individuals. Although the evidence is equivocal, concern over this matter has led the U.S. Food and Drug Administration (2004) to issue an advisory regarding worsening depression and suicidality for patients of all ages.

Absent any reliable means of identifying those individuals who are at greatest risk for experiencing such treatment-emergent adverse events (TEAEs), patients and prescribing doctors face uncertainty in how best to heed warnings of these potential risks of antidepressant treatment. The ability to identify those patients at highest risk for treatment-emergent worsening of suicidality and other adverse effects is an important unmet need.

Several studies have suggested associations between clinical symptoms of depression and treatment-emergent worsening of suicidality, but those results have been controversial and none has demonstrated clinically useful predictive capability for any clinical or biological indicator. In another area, a line of research has focused on brain functional biomarkers of treatment response in major depressive disorder (MDD) (Drevets et al 2002; Leuchter et al 1997, 2005; Mayberg et al 1997, 2000, 2003; Cook and Leuchter 2001; Cook et al 2002, 2005). However, (with two exceptions, i.e., Hunter et al, 2005 and Iosifescu et al, 2005), this work has focused on biomarkers of response or remission, and not for adverse side effects. Currently, clinicians are not able to identify who among their depressed patients is at risk for worsening suicidality or other adverse effects during antidepressant treatment.

There is a great deal of heterogeneity in pharmacotherapy outcomes and, as yet, no proven reliable means of predicting how an individual patient will fare during a given antidepressant treatment regimen. Whereas a great deal of research has focused on predicting dichotomous outcomes (e.g., response vs. non-response) at a primary endpoint, such outcomes do not address other clinically relevant issues related to the course of symptom changes prior to the endpoint. Of particular interest are patients who may experience either transient worsening of symptoms, i.e. "symptom volatility," or more sustained clinical worsening, especially in the first few months after beginning antidepressant treatment.

It is therefore desirable to have methods, apparatus, and systems for efficiently and accurately identifying individuals at risk for adverse effects from psychotropic or CNS-active drugs.

BRIEF SUMMARY

Embodiments of the present invention provide methods, apparatus, and systems for efficiently and accurately identifying individuals at risk for adverse effects from psychotropic or CNS-active treatment. Changes in the biological indicator (e.g. EEG cordance) are used to predict the adverse effects of medication based on an experimentally derived cutoff value. In one embodiment, a reliable biological indicator is provided with high predictive capability for identifying, very early in the course of treatment (e.g. <=48 hours after start of drug treatment), those individuals who are at greatest risk for worsening suicidality and other adverse effects of psychotropic or CNS-active (e.g. antidepressant) treatment. An adverse effect or event is any adverse change in mental or physical health or any "side-effect" that occurs in a person during treatment or within a pre-specified period after dosing is complete. The adverse effects are presumed to be caused by the treatment given their predicted occurrence of being after treatment has begun. Note that actual causality of the adverse effects is not required.

According to one exemplary embodiment, a method of identifying subjects at risk for adverse effects from a psychotropic or CNS-active treatment is provided. A first set of physical values, which are obtained by measuring physical properties of a subject's brain activity at a first time, are received. The first time is before the subject begins treatment. A first resultant value is calculated from a function using the first set of physical values as inputs. A second set of physical values are obtained at a second time that is after the subject begins treatment. A second resultant value of the function is calculated using the second set of physical values as input values. A change in the function from the first time to the second time is calculated from a difference between the first and second resultant values. The difference is compared to a value or values to determine the probability or likelihood of an adverse event. Based on the comparison, it is determined whether the subject is at risk for a future adverse effect from the treatment.

In one embodiment, electroencephalography is used to measure the brain activity. In one aspect, the cordance is used as the function. Specifically, the midline and right frontal cordance (MRFC) may be used. The physical properties may include a voltage at electrodes fp2, af2, f4, f8, fz, and fpz.

These electrodes may be the only electrodes used. In another embodiment, the physical properties of the brain activity are limited to theta waves for the measurement and/or for the resultant value of the function.

In one embodiment, the second time is less than or equal to about 48 hours after treatment begins. In another embodiment, the second time is 72 hours, one week, or one or more months after treatment begins or any time before or while the full therapeutic effects have been realized. In yet another embodiment, the second time is after the first time, but before treatment begins. In another embodiment, the second time is after treatment has ended. The psychotropic or CNS-active treatment may include administering antidepressant drugs or drugs to treat bipolar disorder, anxiety disorders, or psychotic disorders. In another embodiment, the adverse effects include at least one of depressed mood, anxiety, hostility, and suicidal ideation.

In one embodiment, the cutoff value is determined as follows. Data of mood and brain activity properties are acquired at a plurality of different times from a plurality of subjects. At least one time is before treatment and one time is after treatment. A cluster analysis is used to determine optimal physical properties of the subjects' brain activity. Changes in values of the physical properties are examined among the different times. Logistic regression is run to assess association between changes in mood data and optimal physical properties. A cutoff value is determined when an association is identified.

According to another exemplary embodiment, an information storage medium having a plurality of instructions adapted to direct an information processing device to perform an operation for identifying subjects at risk for adverse effects from a psychotropic or CNS-active treatment is provided. The operation includes receiving a first set of physical values from measuring physical properties of a subject's brain activity at a first time, which is before the subject begins treatment; calculating a first resultant value of a function using the first set as inputs; receiving a second set of physical values from measuring the brain activity at a second time, which is after the subject begins treatment; calculating a second resultant value of the function using the second set as inputs; calculating a difference value between the first and second resultant values; comparing the difference value to a cutoff value; and determining whether the subject is likely to have a future adverse effect from the treatment based on the comparison.

According to another exemplary embodiment, a system for predicting adverse antidepressant effects is provided. Sensors measures physical properties of a subject's brain activity. A computing system is coupled with the sensors to analyze the measured values of the physical properties to obtain a difference value of a function of the measured values at different times. The difference value is compared to a cutoff value to determine whether the subject is likely to have a future adverse effect from the treatment.

In one embodiment, a data acquisition system is coupled to the sensors and coupled to the computing system. The data acquisition system converts measured signals to values usable by the computing system. In another embodiment, the sensors are electrodes that measure electromagnetic impulses on the subject's head. In one aspect, the physical properties include a voltage at electrodes fp2, af2, f4, f8, fz, and fpz, which may be the only electrodes analyzed.

A better understanding of the nature and advantages of the present invention may be gained with reference to the following detailed description and the accompanying drawings.

BRIEF DESCRIPTION OF THE DRAWINGS

FIG. 4 shows a table illustrating rates of worsening adverse mood symptoms in healthy and depressed subjects randomized to medication or placebo according to an embodiment of the present invention.

FIGS. 6A and 6B respectively show tables illustrating the results of logistic regression analyses using 48-hour change in MRFC to predict worsening mood symptoms in subjects treated with antidepressant medication or placebo according to an embodiment of the present invention.

FIG. 7A-7C shows ROC curves for 48-hour change in MRFC as a predictor of specific worsening moods in healthy or MDD subjects randomized to antidepressant medication according to an embodiment of the present invention.

DETAILED DESCRIPTION OF THE INVENTION

Figure 1:
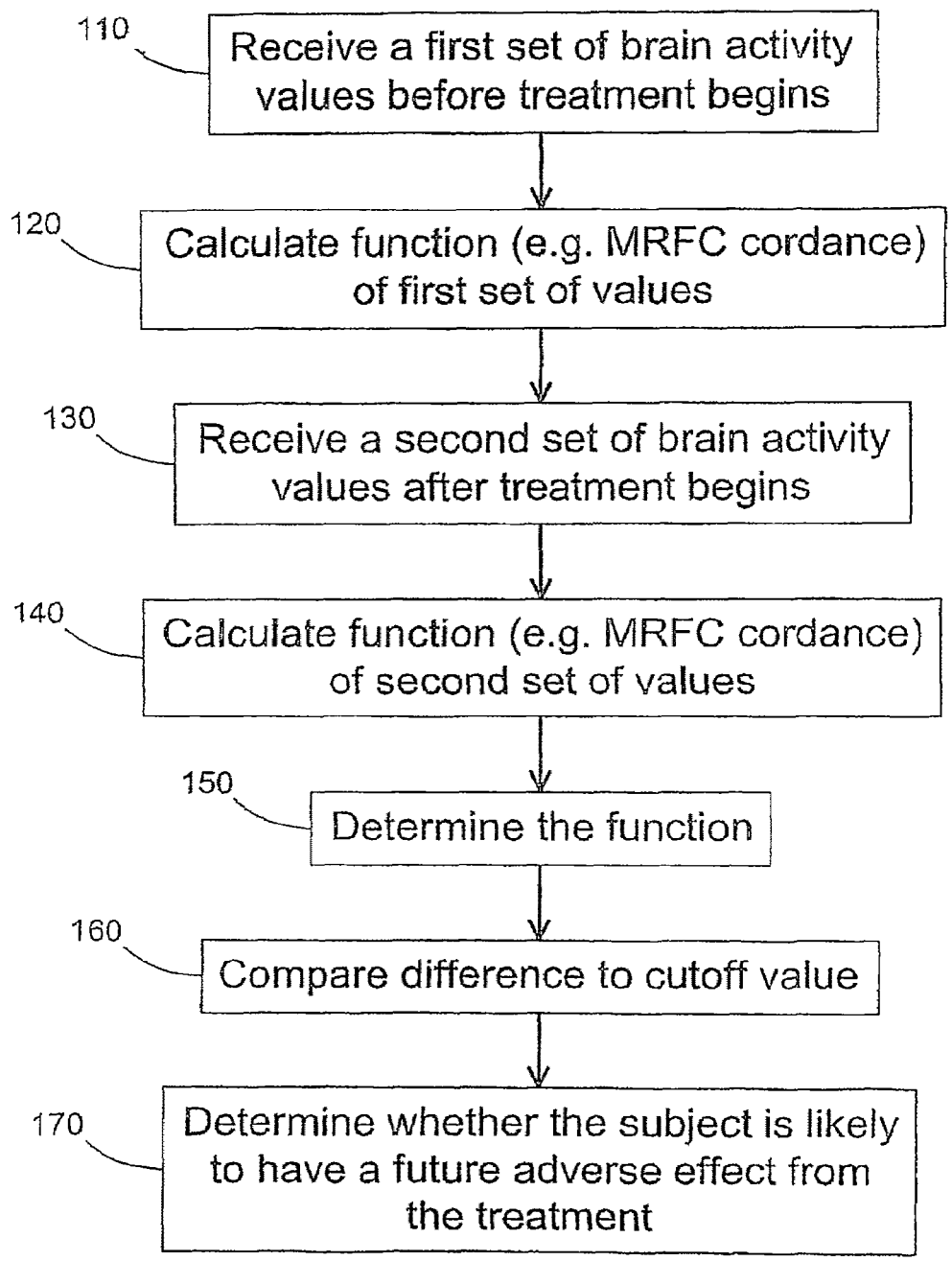
FIG. 1 is a flow diagram illustrating a method for identifying individuals at risk for adverse effects from psychotropic drugs according to an embodiment of the present invention.

Embodiments of the present invention provide methods, apparatus, and systems for efficiently and accurately identifying individuals at risk for adverse effects from psychotropic or CNS-active treatment. Changes in the biological indicator (e.g. EEG cordance) are used to predict the adverse effects of medication. In one embodiment, a reliable biological indicator is provided with high predictive capability for identifying, very early in the course of treatment (e.g. <=48 hours after start of drug treatment), those individuals who are at greatest risk for worsening suicidality and other adverse effects of antidepressant treatment and treatment for other psychiatric disorders.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"A psychotic disorder" refers to a condition that affects the mind, resulting in at least some loss of contact with reality. Symptoms of a psychotic disorder include, e.g., hallucinations, changed behavior that is not based on reality, delusions and the like. See, e.g., DSM IV. Schizophrenia, schizoaffective disorder, schizophreniform disorder, delusional disorder, brief psychotic disorder, substance-induced psychotic disorder, and shared psychotic disorder are examples of psychotic disorders.

"Schizophrenia" refers to a psychotic disorder involving a withdrawal from reality by an individual. Symptoms comprise for at least a part of a month two or more of the following symptoms: delusions (only one symptom is required if a delusion is bizarre, such as being abducted in a space ship from the sun); hallucinations (only one symptom is required if hallucinations are of at least two voices talking to one another or of a voice that keeps up a running commentary on the patient's thoughts or actions); disorganized speech (e.g., frequent derailment or incoherence); grossly disorganized or catatonic behavior; or negative symptoms, i.e., affective flattening, alogia, or avolition. Schizophrenia encompasses disorders such as, e.g., schizoaffective disorders. Diagnosis of schizophrenia is described in, e.g., DSM IV. Types of schizophrenia include, e.g., paranoid, disorganized, catatonic, undifferentiated, and residual.

An "antidepressant" refers to an agents typically used to treat clinical depression. Antidepressants includes compounds of different classes including, for example, specific serotonin reuptake inhibitors (e.g., fluoxetine), tricyclic antidepressants (e.g., desipramine), and dopamine reuptake inhibitors (e.g, bupropion). Typically, antidepressants of different classes exert their therapeutic effects via different biochemical pathways. Often these biochemical pathways overlap or intersect. Additional diseases or disorders often treated with antidepressants include, chronic pain, anxiety disorders, and hot flashes.

I. INTRODUCTION

Quantitative electroencephalography (QEEG), specifically QEEG cordance, can be used to monitor brain changes during antidepressant treatment. QEEG measures are safe, affordable, and clinically viable; QEEG cordance has been shown to have a stronger correlation with regional cerebral blood flow ($^{15}O$ PET) than other QEEG power spectrum measures. Decreases in frontal theta cordance beginning one week after start of antidepressant treatment have been associated with later response or remission (Leuchter et al 1997, Cook and Leuchter 2001, Cook et al 2002, 2005, 2006; Bares et al 2006, Kopecek et al 2006). Because cordance changes associated with medication response are found to be different from those associated with placebo response, they may advantageously be used as unique markers for medication effects.

In one embodiment, a change in midline and right frontal cordance (MFRC) is assessed 48 hours after start of medication as a potential biomarker of worsening mood symptoms. In one study, subjects included 32 healthy and 72 depressed subjects treated with fluoxetine 20 mg, venlafaxine 150 mg, or placebo, in double-blind randomized controlled trials. QEEG recordings were obtained immediately before, and 48 hours after, beginning randomized treatment.

In one embodiment, binary logistic regression analyses is used to examine relationships between 48-hour change in MRFC, and worsening suicidality, depressed mood, anxiety, and hostility as determined by $HamD_{17}$ or SCL-90-R item responses. In depressed subjects treated with medication (n=37), change in MRFC at 48 hours was negatively associated with worsening suicidal ideation (logit coefficient=−1.76, SE=0.83, exact p=0.02) and positively associated worsening depressed mood (logit coefficient=2.30, SE=1.19, exact p=0.03). MRFC change at 48 hours was not associated with worsening in subjects receiving placebo. Results of these analyses suggest that changes in the MRFC measure 48 hours after start of drug may reflect acute pharmacodynamic effects related to worsening mood and suicidal ideation during antidepressant treatment.

Accordingly, embodiments of the invention use a change in value in the MRFC to predict the probability, likelihood or chance of adverse effects in at risk individuals. Thus, in one embodiment, the probability of an adverse event is determined using, e.g., regressive analysis and other analytical methods. In other embodiments, with a properly chosen cutoff value for the difference value between the two times, a change in MRFC can yield high accuracy, for example, 73% accuracy (80% sensitivity, 72% specificity). In one embodiment, a cutoff of about −0.48 cordance units is used as a positive indicator for suicidal worsening. Embodiments of the present invention may also be employed to detect risk for adverse effects from other psychotropic or CNS-active agents used for a variety of medical indications, such as antipsychotic agents (e.g. haloperidol and molindone), anti-obsessive agents (e.g. parozetine), and antianxiety agents (e.g. prazepam and alprazolam), as well as magnetic and electrical brain stimulation procedures (e.g., transcranial magnetic stimulation, vagus nerve stimulation) to treat depression. Although examples are presented with respect to QEEG, other brain imaging techniques can be used.

I. DIAGNOSTIC TEST

This method may be applied in clinical and/or drug development settings. In the clinical setting, this method provides a neurophysiologic marker early in the course of antidepressant treatment, e.g., within two days of initiating antidepressant treatment, that helps: a) determine one's risk of experiencing increased anxiety, agitation, hostility, and/or suicidal ideation with continuation of that medication and b) determine one's risk of experiencing overall clinical worsening of depressive symptoms with continuation of that medication. In the drug development process, this method helps to determine the safety of putative antidepressant (and other psychotropic) compounds at various doses. For example, a test compound that routinely produces a pattern of early EEG changes that is similar to the profile of an adverse reactor (i.e., one who develops increased anxiety, agitation, and/or suicidal ideation during the first few months of antidepressant treatment) may stand a greater chance of posing safety concerns.

FIG. 1 is a flow diagram illustrating a method 100 for identifying individuals at risk for adverse effects from psychotropic drugs according to an embodiment of the present invention. In step 110, a first set of physical values are received, which are obtained by measuring one or more physical properties of a subject's brain activity at a first time. The first time is before the first person begins treatment with an antidepressant. In one embodiment, electroencephalographic (EEG) recordings for an individual are obtained at baseline (T1; prior to the start of drug). In another embodiment, a brain imaging technique other than EEG is used. However, EEG is likely to be the safest and least expensive imaging method.

In step 120, a first resultant value of a function is calculated using the first set of physical values as input values. In one embodiment, from these physical values, a single number is generated that can be used to determine the chance or percent likelihood that the individual will experience medication-related increases in anxiety, agitation, hostility, and/or suicidal ideation with continuation of the specific antidepressant over the subsequent two months. In one embodiment, the EEG output is converted to 'cordance' using the algorithm described in (Leuchter et al 1999) and below. In another embodiment, other quantities may be used besides cordance, such as power spectral arrays, bispectral arrays, and higher-order spectral arrays.

In step 130, a second set of physical values are received, which are obtained by measuring one or more physical properties of a subject's brain activity at a second time. The second time is after the first person begins treatment with an antidepressant. For example, (EEG) recordings for an individual are obtained again within 48 hours or less of an initial daily drug dose (T2). In step 140, a second resultant value of the function is calculated using the second set of physical values as input values. In one embodiment, the function is limited to a particular band of brain waves, for example, theta waves, resulting in a result for theta cordance. In another embodiment, other bands or combination of bands are used.

In step 150, a change in the function from the first time to the second time is determined by calculating a difference value between the first and second resultant values. In one embodiment, a change in theta cordance between T1 and T2 (i.e., T2–T1) is calculated. In another embodiment, other functional combinations of the resultant values may be used. In step 160, the difference value is compared to a cutoff value. In one embodiment, the specified cut-point is selected from an ROC curve as described below. In another embodiment, more than one difference value and cutoff value are used. For example, each adverse effect may have a separate cutoff value. Note that the difference value may be used in a function whose output is compared to a cutoff value, which still results in an equivalent comparison. In one embodiment, the cutoff value is zero. In step 170, based on the comparison, it is determined whether the subject is at risk for a future adverse effect from the treatment. The term "at risk" encompasses any difference value that has been deemed to be appreciable to report. Thus, at a minimum, a binary classification is made. In one embodiment, additional classifications are made. For example, whether the subject is at high risk or very high risk can be made. In one aspect, a specific percentage or range of percentages is provided for a likelihood of a future adverse effect, which effectively provides that a subject is "at risk."

Figure 2:
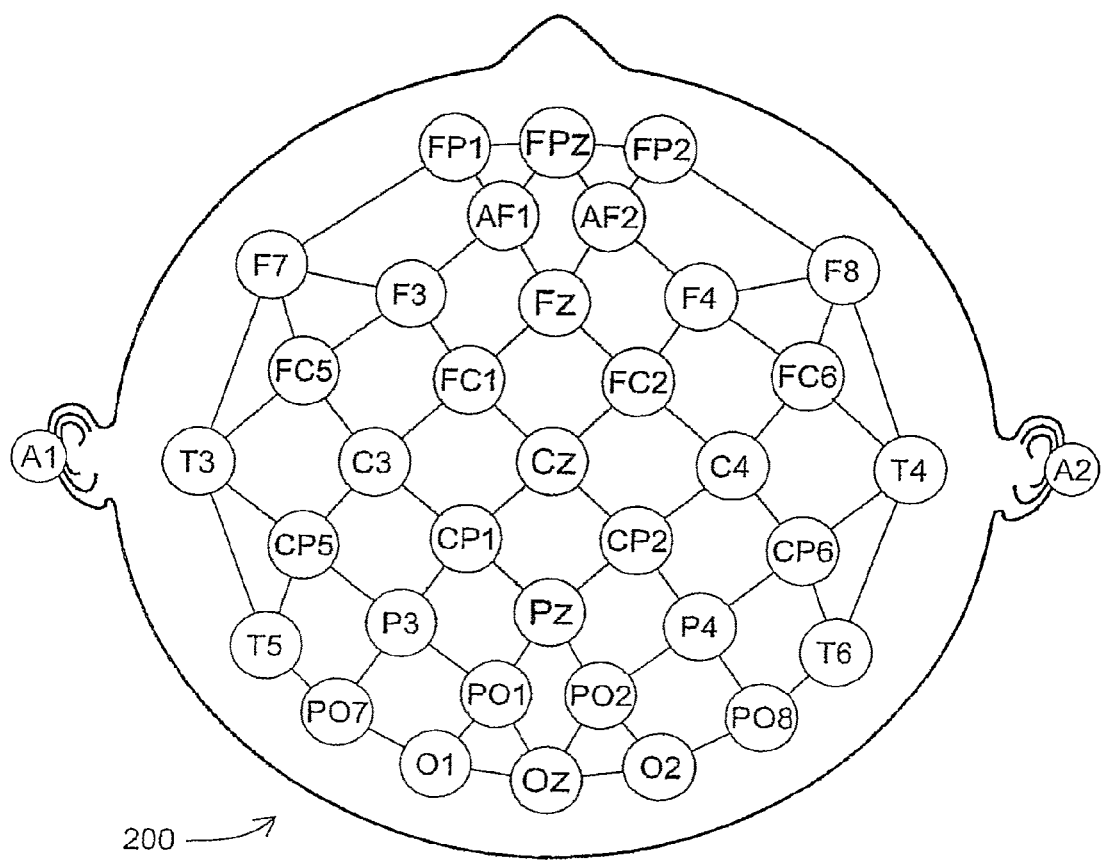
FIG. 2 shows an electrode montage according to an embodiment of the present invention.

In one embodiment, the brain activity of the MRFC is measured. FIG. 2 shows an electrode montage 200 according to an embodiment of the present invention. In one embodiment, measurements of the electrodes fp2, af2, f4, f8, fz, and fpz are used for the physical properties of a subject's brain activity. In one embodiment, the prediction of adverse effects (such as antidepressant-emergent suicidality) with EEG disturbances also uses a constellation of other clinical mechanisms.

II. FORMULATING DIAGNOSTIC METHOD

Figure 3:
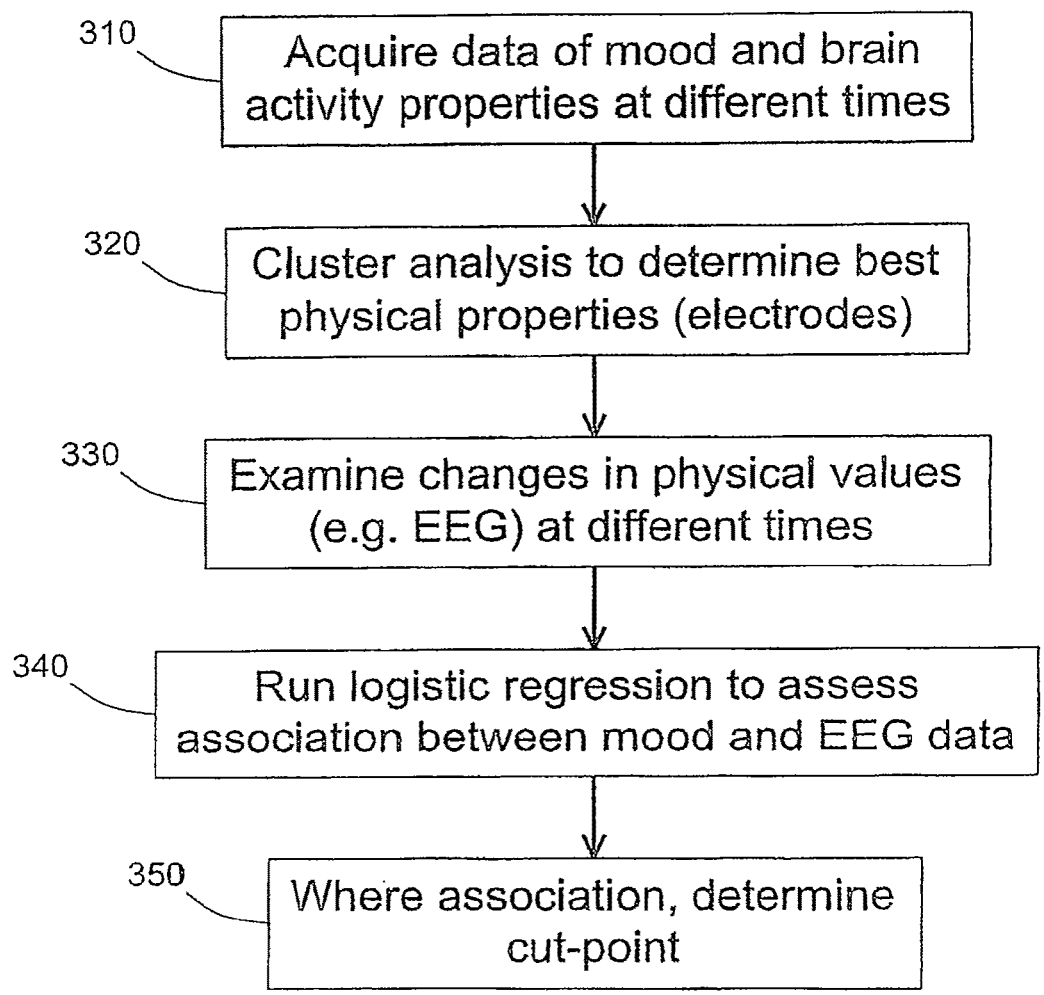
FIG. 3 is a flow diagram of a method for creating a diagnostic method for identifying individuals at risk for adverse effects from psychotropic drugs according to an embodiment of the present invention.

FIG. 3 is a flow diagram of a method 300 for creating a diagnostic method for identifying individuals at risk for adverse effects from psychotropic drugs according to an embodiment of the present invention. In step 310, data is acquired. In one aspect, one type of data is the mood data that is to be predicted and the other type of data is the brain activity properties that are to predict the mood data.

In step 320, a cluster analysis is performed to determine the best physical properties, such as which electrodes to use. In step 330, changes in the physical values of the physical properties (electrodes) are examined at different times. In step 340, a logistic regression is run to assess an association between the mood data and the brain activity (EEG) data. In step 350, when an association is found, a cut-point is determined, e.g. using ROC curves.

In one embodiment, the method was created using EEG data pooled from depressed individuals treated with fluoxetine or venlafaxine (n=25), and healthy individuals treated with venlafaxine (n=17). Subjects were categorized as either worseners or non-worseners in terms of changes in their anxiety, agitation, hostility, and suicidal ideation, commensurate with antidepressant treatment. Regional changes in brain function occurring 48 hours after daily dosing were compared for those who eventually did versus did not experience worsening.

Among normal healthy subjects, anxiety worseners and hostility worseners were found to exhibit greater decreases in QEEG cordance in the right frontal region (fp2, af2, f4, f8, fz, fpz) than non-worseners, p=0.06 and p=0.009, respectively. In depressed patients, those with increases in agitation or suicidal ideation after initiation of antidepressant medication showed greater decreases in QEEG cordance in the same right frontal region p=0.025 and p=0.0005, respectively. In one embodiment, a receiver operating curve is used to select an optimal cut-point to predict adverse medication effects based upon the degree of change in right frontal cordance within 48 hours of daily dosing.

A. Acquiring of Data

1. Mood Data

In an exemplary study, subjects received one week of single-blinded treatment with placebo prior to eight weeks of randomized double-blinded treatment with medication (fluoxetine 20 mg or venlafaxine 150 mg; n=37) or placebo (n=35). In one embodiment, venlafaxine was dosed at 37.5 mg/day to start with and increased to achieve 150 mg after 10 days); fluoxetine dosing was constant at 20 mg/day. Placebo was administered on the same schedule as active drug within each trial to preserve blinding. Clinical symptoms were assessed at: baseline, end of placebo lead-in, and at 48 hours, 1 week, 2 weeks, 4 weeks, and 8 weeks after randomization. Through week 4, the clinical assessment timepoints mirrored those in the 4-week study of healthy subjects; an additional (week 8) assessment was evaluated in the MDD trials. Adverse mood symptoms were assessed using items from the $HamD_{17}$ and the Symptom Checklist-90-R (SCL-90-R) (Derogatis 1994). Subjects were characterized as worseners or non-worseners with respect to each of these adverse mood symptoms.

In one embodiment, potential antidepressant-emergent worsening was identified. A worsening was determined by comparing mood ratings during antidepressant treatment, to mood ratings obtained prior to the start of medication. For each symptom, medication subjects who had a worse rating at any post-randomization timepoint, as compared to both baseline and end of placebo lead-in, were classified as worseners. For use as a comparison group, subjects randomized to placebo were also classified as worseners or non-worseners using the same criteria as described for the medication subjects; those who had worse adverse mood ratings at any post-randomization timepoint as compared to baseline and end of placebo lead-in were classified as worseners. Differences in rates of worsening mood symptoms for subjects randomized to medication versus placebo were assessed using Fisher's Exact Test.

FIG. 4 shows a table 400 illustrating rates of worsening adverse mood symptoms in healthy and depressed subjects randomized to medication or placebo according to an embodiment of the present invention. Table 400 shows the percentages of healthy subjects (top) and MDD subjects (bottom) who experienced worsening adverse mood symptoms during randomized treatment. Healthy subjects randomized to medication versus placebo were not found to have significantly different rates of worsening anxiety, hostility, or depressed mood. None of the healthy non-depressed subjects reported suicidal ideation at any point during the trial. Among MDD subjects, there were no significant differences in rates of worsening between medication- and placebo-treated groups. Worsening suicidal ideation in the MDD sample was reported in 13.5% of subjects treated with medication and in 22.9% of subjects treated with placebo. Across all timepoints, the severity of suicidal ideation as measured using $HamD_{17}$ item #3 ranged from '0' (absent) to '3' (suicide ideas or gesture). No suicide attempt was made by any subject during enrolled study treatment.

Of the five MDD subjects who reported worsening suicidal ideation during medication treatment, three suicidal-ideation-worseners also reported worsening anxiety, one suicidal-ideation-worsener reported worsening depressed mood and hostility, and one suicidal-ideation-worsener did not report worsening in any other symptom. Two of the five suicidal ideation worseners met criteria for clinical response ($HamD_{17} \leq 10$) at the end of eight weeks treatment.

Worsening depressed mood, anxiety, hostility, or suicidal ideation were observed at some point during treatment in 57% of depressed subjects randomized to antidepressant medication and in 60% of subjects randomized to placebo. A small proportion of MDD subjects randomized to antidepressant treatment (5 of 37 subjects; 13.5%) expressed worsening suicidal ideation. These seemingly high rates of worsening are not surprising considering that the criterion was any amount of worsening at any timepoint assessed over four or eight weeks of randomized treatment. Fluctuations of these adverse mood symptoms are characteristic of MDD and, exclusive of suicidal ideation, are also to be expected in healthy non-depressed persons. There were no statistically significant differences in rates of worsening between medication- and placebo-treated subjects. However, exploratory findings from the present study suggest that early pharmacodynamic effects on the EEG may have been related to worsening of some antidepressant-emergent symptoms.

With respect to outcome measures, we examined categorical (worsener vs non-worsener) outcomes that do not account for degree of symptom change. For some mood symptoms, worsening was determined on the basis of a single item. For example, worsening suicidal ideation was based upon response to item #3 on the $HamD_{17}$, which has been shown to correlate strongly with the Beck Scale for Suicidal Ideation (Beck et al 1997). In one embodiment, measures developed specifically to evaluate the severity of suicidal ideation and suicide risk are used. No subject in this study attempted or completed suicide. In other embodiments, other emergent mood/behavioral effects may be measured, such as other symptoms from the $HamD_{17}$, e.g. insomnia, agitation, and weight-loss. The adverse effects may also be symptoms not covered by the $HamD_{17}$ or SCL-90-R checklists.

B. QEEG Data

In one embodiment, midline-and-right-frontal cordance (MRFC), was derived by averaging cordance values from adjacent electrodes FPz, Fz, FP2, AF2, F4, and F8 as shown in FIG. 2. We examined change in MRFC from end of placebo lead-in (the timepoint just prior to start of drug) to 48 hours after randomization (the first EEG observation after start of drug). In one aspect, the MRFC change over this interval can distinguish pharmacodynamic effects of antidepressant from placebo. We subtracted the MRFC cordance value at the end of placebo lead-in from the cordance value at 48 hours to determine change in MRFC.

Here, relationships between change in MRFC 48 hours after start of drug, and worsening suicidality and mood symptoms were examined. In one embodiment, it is determined whether early central nervous system (CNS) effects of antidepressant medication, as captured using QEEG cordance, might be related to the later emergence of specific adverse mood symptoms, such as worsening suicidal ideation, depressed mood, anxiety, and hostility. Data was examined from placebo-controlled antidepressant treatment trials for two groups of subjects: normal healthy adults, and adults with major depressive disorder (MDD).

Figure 5:
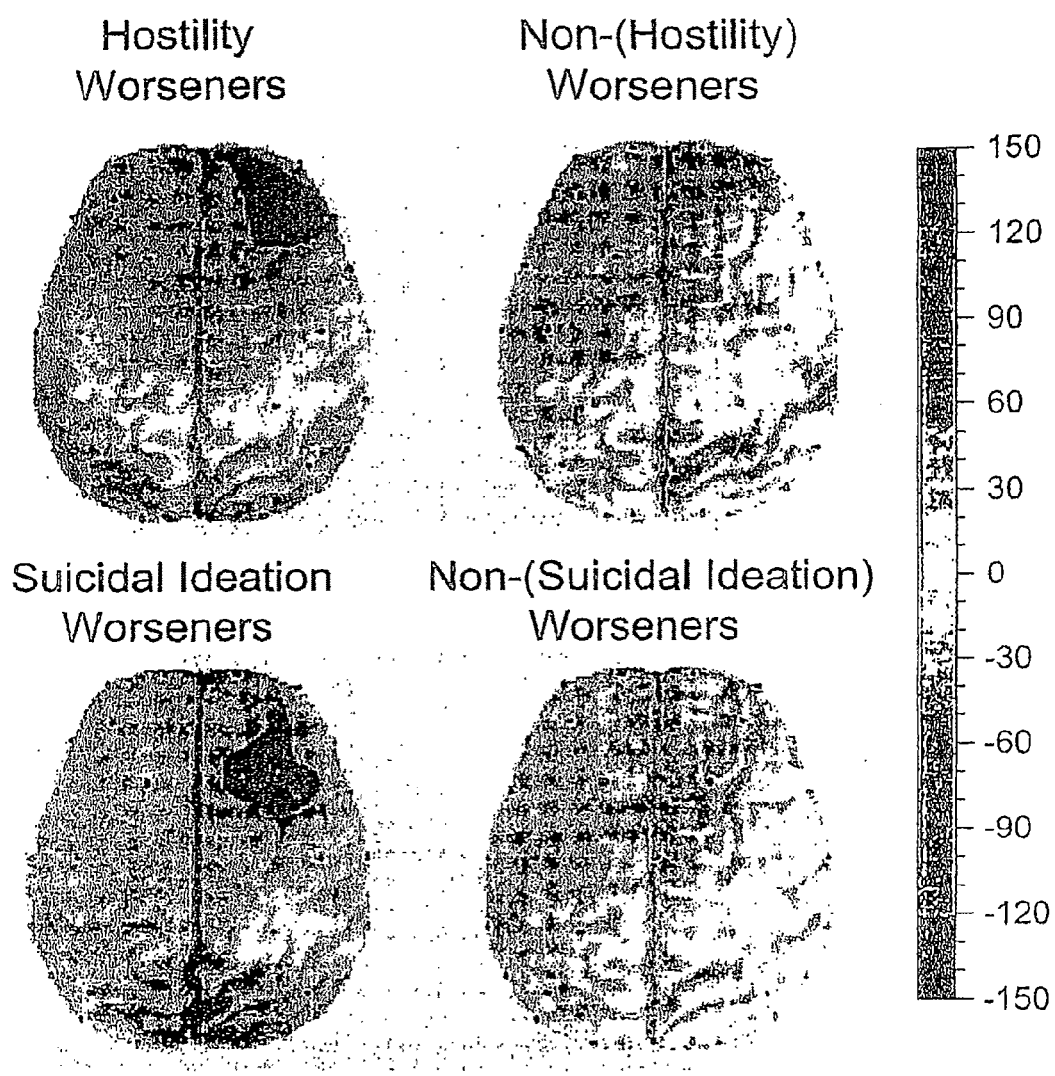
FIG. 5 shows cordance changes 48 hours after start of drug for healthy non-depressed subjects with antidepressant-emergent hostility (top panel), and for MDD subjects with antidepressant-emergent suicidal ideation (bottom) according to an embodiment of the present invention.

FIG. 5 shows cordance changes 48 hours after start of drug for healthy non-depressed subjects with antidepressant-emergent hostility (top panel), and for MDD subjects with antidepressant-emergent suicidal ideation (bottom) according to an embodiment of the present invention. Baseline MRFC values did not differ significantly between worseners and non-worseners and were not significantly associated with any worsening mood symptoms in healthy or depressed subjects. Change in MRFC did not approach statistical significance as a predictor of worsening for any mood symptom among healthy or depressed subjects randomized to placebo.

In one embodiment, EEG changes at timepoints earlier than 48 hours after start of drug could further develop the invention. It is possible that region- and frequency-specific changes in the EEG (e.g. change in midline and right frontal theta cordance; MRFC) observed earlier than 48 hours after start of drug might have a predictive capability equal to or greater than the 48-hour QEEG biomarker. For example, EEG changes shortly following an initial single dose might predict later adverse effects of medication, thereby making it possible to test the medication within the timeframe of a single medical visit.

B. Clustering

In one embodiment, hierarchical cluster analysis is used to identify the inter-correlated electrodes that comprise MRFC. The cluster analysis determined those electrodes that best distinguish EEG changes resulting from brief treatment with a specific medication or class of medications as compared to placebo. Change in MRFC 48 hours after beginning randomized treatment significantly distinguished between medication and placebo exposure. This procedure may be used for antidepressant or other CNS-active medications for which there is some concern over adverse effects on suicidality or other aspects of mood or behavior.

Changes in midline-and-right-frontal cordance (MRFC) 48 hours after start of drug showed a specific relation to later antidepressant-emergent worsening. In normal healthy subjects, we noted a trend finding (exact $p<0.1$) linking MFRC change to worsening hostility. In depressed subjects, change in MFRC was a significant predictor (exact $p<0.05$) for two of four worsening mood symptoms: worsening depressed mood and suicidal ideation. A similar physiologic pattern, i.e., a large decrease in MRFC, was shown to underlie worsening hostility in healthy subjects and worsening suicidal ideation in depressed subjects (see FIG. 5) suggesting that this similar drug-induced exacerbation of the EEG may have variant behavioral manifestations in depressed versus non-depressed persons. Surprisingly, among MDD subjects, whereas large decreases in MRFC predicted worsening suicidal ideation, large increases in MRFC predicted worsening depressed mood.

Embodiments may identify other neurotransmitter systems via the cluster analysis, such as the anterior cingulate cortex. In one embodiment, different region- and frequency-specific change in the EEG are used to achieve predictive capability as has been shown for MRFC. In another embodiment, cluster analysis techniques are used to identify regional EEG changes using measures other than cordance (e.g., non-proprietary absolute and/or relative power), and examining frequencies outside of the theta band (5-8 Hz) that might better predict adverse effects of antidepressant medications.

C. Changes in EEG

In one embodiment, changes in the EEG are examined at timepoints<48 hours after start of medication. The changes of various frequency bands and EEG measures (e.g., relative power, absolute power, cordance) may be examined. In one aspect, the region- and frequency-specific EEG measures that show the best separation of CNS effects of drug versus placebo are determined.

D. Regression

In one embodiment, logistic regression analyses are run to assess the association between changes in the identified EEG measures at the specified timepoint, and clinical status (worsener versus non-worsener) at any point during the first 8 weeks of treatment with respect to suicidality, hostility, anxiety, and/or other adverse effects of interest. The predictive relationships between 48-hour change in MRFC and worsening of specific adverse mood symptoms may be explored using binary logistic regression analyses.

In one embodiment, the regression models consisted of 48-hour change in MRFC as the single independent variable. Separate analyses were conducted for each specific adverse mood symptom in four groups: healthy subjects taking medication, healthy subjects taking placebo, depressed subjects taking medication, and depressed subjects taking placebo. We hypothesized that MRFC might predict worsening among medication-treated subjects but not among placebo-treated subjects. Because of the small sample sizes and cell sizes we used an exact method to determine p-values (LogXact 4.0; Statistical Solutions, Saugus, Mass.). For models that showed a trend toward statistical significance ($p<0.1$) we calculated predicted probabilities using a standard formula, and conducted receiver operating characteristic (ROC) analysis using SPSS 11.0 for Mac OS X.

FIGS. 6A and 6B respectively show tables 600 and 650 illustrating the results of logistic regression analyses using 48-hour change in MRFC to predict worsening mood symptoms in subjects treated with antidepressant medication (600) or placebo (650) according to an embodiment of the present invention. In normal healthy subjects receiving medication, the model using 48-hour change in MRFC to predict worsening hostility (5 of 17 subjects) approached statistical significance (exact $p=0.09$) with a trend relationship between decreases in MRFC and greater probabilities of worsening. For example, using predicted probabilities, when the MRFC change value is 0, the probability of being a hostility worsener is 0.11. However, when the MFRC change value is −1, the probability increases to 0.35, and at an MFRC change value of −2, the probability of being a hostility worsener is 0.71

In depressed subjects treated with medication, 48-hour change in MRFC predicted worsening suicidal ideation (5 of 37 subjects; exact $p<0.02$) and worsening depressed mood (3 of 37 subjects; exact $p=0.03$). With respect to suicidal ideation, decreases in MRFC predicted worsening. For example, as the value of MRFC changes from −1 to −2, the probability of worsening suicidal ideation increases from 0.27 to 0.70.

E. Determine Cut-Points

In one embodiment, where there is a significant association, receiver operating characteristic analysis is used to determine a cutoff value for the EEG indicator variable that provides the most clinically useful balance of sensitivity, specificity and overall accuracy in predicting the adverse effects of interest.

Figure 7A:
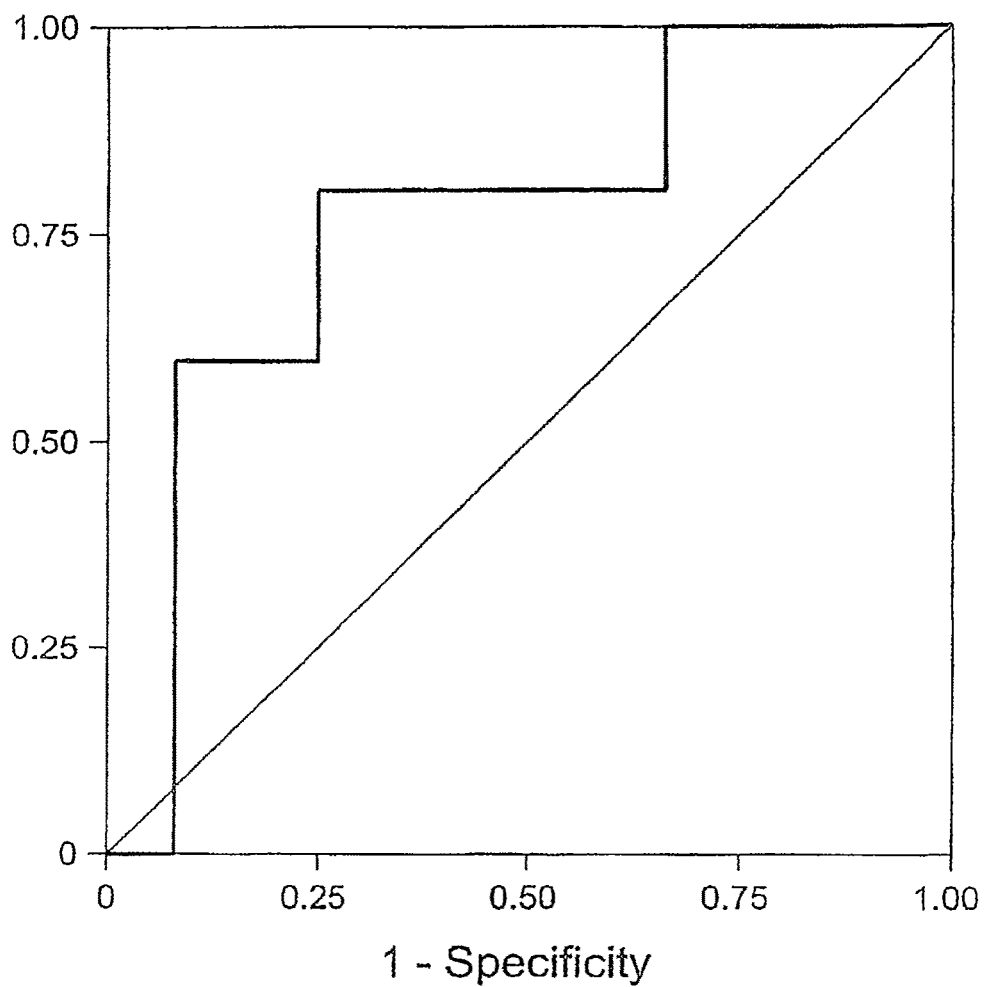

For table 600, MRFC predicted worsening hostility in normal subjects with 76% accuracy (80% sensitivity, 75% specificity) and 0.77 area under the Receiver Operating Characteristic (ROC) curve (FIG. 7). FIG. 7A shows an ROC curve for 48-hour change in MRFC as a predictor of worsening hostility in healthy subjects randomized to antidepressant medication according to an embodiment of the present invention. Hostility worseners showed a mean decrease in MFRC of −1.16 (SD=0.67) cordance units, as compared to non-worseners who showed a mean decrease of −0.50 (SD=0.66) cordance units.

Figure 7B:
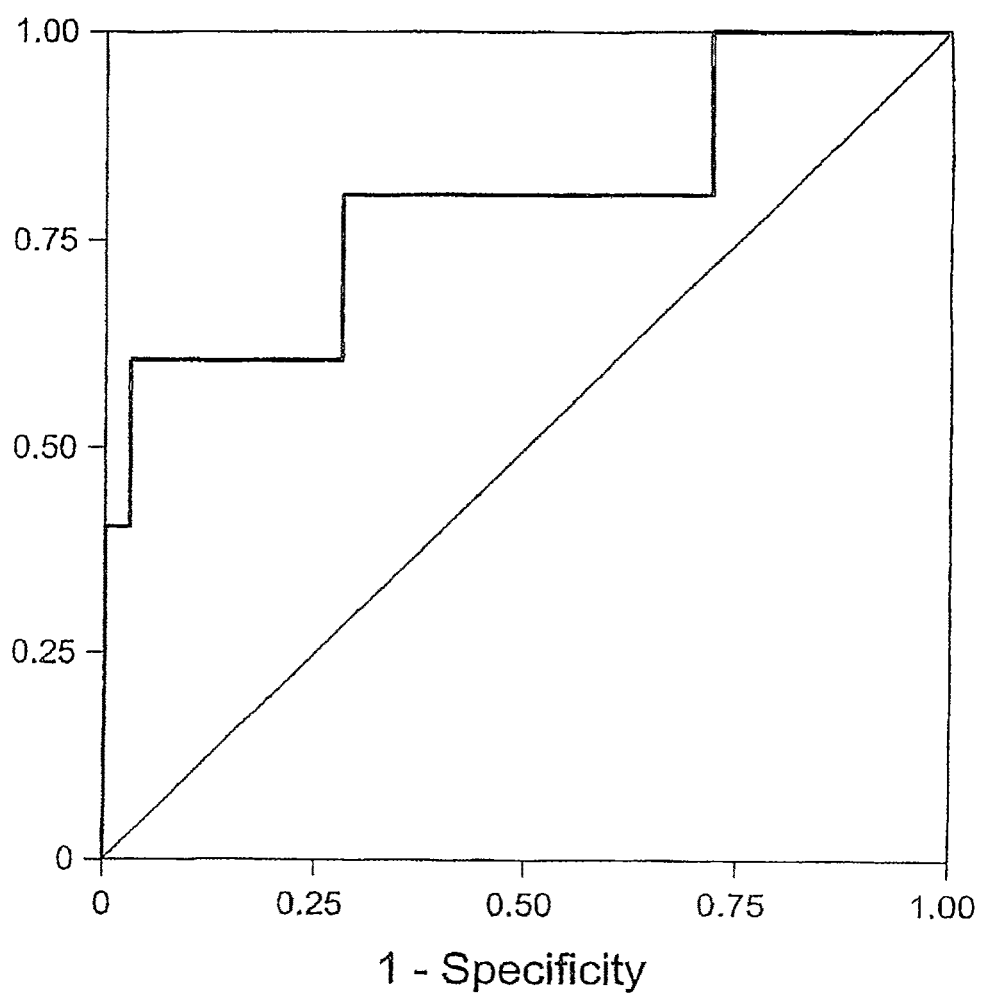

For table 650, Change in MRFC yielded 73% accuracy (80% sensitivity, 72% specificity) and 0.79 area under the ROC curve (FIG. 3). FIG. 7B shows an ROC curve for 48-hour change in MRFC as a predictor of worsening suicidal ideation in MDD subjects randomized to antidepressant medication according to an embodiment of the present invention. Suicidal-ideation-worseners showed a mean decrease in MFRC of −1.00 (SD=0.91) cordance units as compared to non-worseners who showed a mean decrease of −0.16 (SD=0.69) cordance units.

For depressed mood, increases in MRFC predicted worsening. For example, as the value of MRFC changes from 1 to 2, the probability of worsening depressed mood increases from 0.37 to 0.85. Change in MRFC predicted worsening depressed mood with 73% accuracy (100% sensitivity, 71% specificity) and 0.88 area under the ROC curve (FIG. 4). FIG. 7C shows an ROC curve for 48-hour change in MRFC as a predictor of worsening depressed mood in MDD subjects randomized to antidepressant medication according to an embodiment of the present invention. Depressed mood worseners had a mean increase of 0.65 (SD=0.55) cordance units, and non-worseners had a decrease of –0.35 (SD=0.73) cordance units.

In other embodiments, the likelihood, chance or probability of an adverse effect is determined by comparison of EEG values at two time points using regression analysis or other analytical methods.

III. SYSTEM

Figure 8:
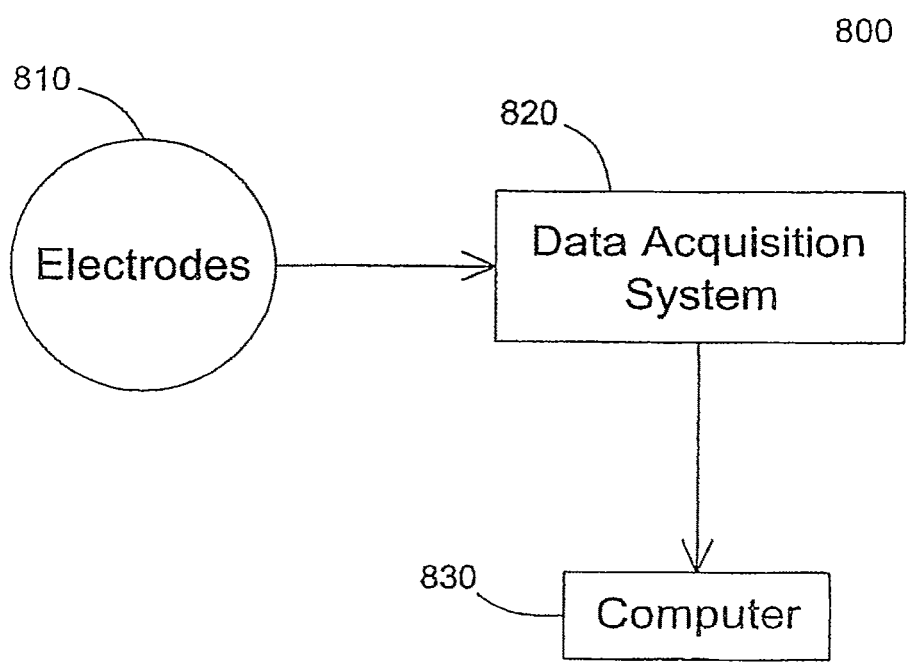
FIG. 8 illustrates a system for identifying individuals at risk for adverse effects from psychotropic drugs according to an embodiment of the present invention.

FIG. 8 illustrates a system 800 for identifying individuals at risk for adverse effects from psychotropic drugs according to an embodiment of the present invention. Electrodes 800 receive electromagnetic signals from a subject. The electrodes may be in the orientation of montage 200. The signals are recorded or otherwise processed by data acquisition system 820. A computing system 830 analyzes the data according to embodiments of the present invention. Thus, in one embodiment, methods and related reports of assessed risk are incorporated into a user-friendly software package designed for use with standard or specialized EEG computing/recording equipment. In one embodiment, to minimize potential unauthorized use of the invention, data is transferred to a central hub connected to computer 830 for assessment and results.

IV. CONCLUSIONS

Those antidepressant-treated subjects who showed apparent mood/behavioral sensitivity to drug (i.e., worsening depressed mood, hostility, or suicidal ideation) had increased central nervous system (CNS) sensitivity to drug as demonstrated by greater absolute changes in MRFC at 48 hours. Large decreases in MRFC were linked to hostility (trend) and suicidal ideation, whereas large increases were linked to depressed mood. In one aspect, exaggerated MRFC changes in either direction may reflect pharmacodynamic perturbations that have untoward consequences for the emergence of worsening adverse mood symptoms during antidepressant treatment.

Both of the antidepressant medications used in this study inhibit serotonin reuptake; fluoxetine is a selective serotonin reuptake inhibitor (SSRI) whereas venlafaxine inhibits primarily serotonin reuptake at 37.5 mg (the 48-hour dose in this study) and also inhibits norepinephrine reuptake at 150 mg (the full daily dose delivered after 10 days). In one aspect, these pharmacodynamic/pharmacokinetic differences might influence the region or timecourse of EEG changes, e.g. requiring different timepoints and different cut-points. In another aspect, change in MRFC 48 hours after start of drug may reflect a primary serotonin response and/or downstream effects on other neurotransmitter systems including those having primary excitatory and inhibitory effects, i.e., glutamate and gamma-aminobutyric acid (GABA).

Additionally, although a common clinical observation may be the co-occurrence of worsening mood and suicidal ideation, these data raise the possibility that, in the context of antidepressant-emergent adverse events, worsening suicidal ideation and worsening mood do not comport. It is possible that antidepressant-emergent suicidal ideation on one hand, and worsening depressed mood on the other, are characterized by physiologically distinct mechanisms. In this dataset, antidepressant-emergent worsening of suicidal ideation (as measured using $HamD_{17}$ item #3) did not appear to track with worsening depressed mood (as measured using $HamD_{17}$ item #1). Only 1 subject reported both worsening suicidal ideation and worsening depressed mood. Moreover, worsening of suicidal ideation during antidepressant treatment did not preclude a good overall clinical outcome. Two of the five persons with worsening suicidal ideation met criteria for response ($HamD_{17} \leq 10$) at the end of eight weeks of treatment.

EXAMPLES

The following examples are offered to illustrate, but not to limit the claimed invention.

Materials and Methods

Overview

We examined data from subjects who completed one of four double-blind placebo-controlled antidepressant treatment trials at the University of California Los Angeles (UCLA) Laboratory of Brain, Behavior and Pharmacology, an outpatient research facility. Protocols included EEG recordings and clinical assessments obtained at common timepoints across trials. Separate analyses were conducted for normal healthy subjects who participated in a four-week randomized trial, and MDD subjects who participated in one of three eight-week randomized trials. All subjects were treated in accordance with ethical standards set forth in the Declaration of Helsinki. Experimental procedures were approved by the UCLA Institutional Review Board and were explained fully to the subjects before obtaining written informed consent.

Subjects and Experimental Procedures

For the normal healthy subjects, thirty-two healthy never-depressed adults completed a single randomized trial and were compensated for their participation. Subjects were recruited by community advertisement and were screened using a standard clinical evaluation, a structured clinical interview (Structured Clinical Interview for Axis I DSM-IV Disorders—Patient Edition: SCID-I/P, version 2.0) (First et al 1996) and the 17-item Hamilton Depression Rating Scale ($HamD_{17}$) (Hamilton 1960). Exclusion criteria included: prior use of antidepressant medication, meeting DSM-IV axis I criteria for a current or past mood, anxiety, cognitive, or psychotic disorder on the basis of the SCID-I/P interview, or meeting criteria for a cluster A or B axis II diagnosis that was sufficiently severe to interfere with completion of the protocol. Subjects were excluded if they had any illness or condition known to affect brain function or to contraindicate the use of venlafaxine. Participants were required to abstain from using sedative-hypnotics, or other medications with significant central nervous system (CNS) activity throughout the study and for ten days prior to entering. Urine toxicology screens were performed to rule out psychoactive medication use.

Subjects received one week of single-blinded treatment with placebo prior to four weeks of randomized double-blinded treatment with venlafaxine (n=17) or placebo (n=15). Dosing began at 37.5 mg/day with an increase of 37.5 mg every three days to achieve 150 mg after 10 days. Look-alike placebo capsules were administered on the same schedule. Clinical symptoms were assessed at: baseline, end of placebo lead-in, and at 48 hours, 1 week, 2 weeks and 4 weeks after randomization.

For depressed subjects, seventy-two subjects with MDD completed one of three independent placebo-controlled randomized treatment trials. The trials utilized identical recruitment procedures, inclusion/exclusion criteria, and design features except for the active medication. Subjects enrolled in the three trials did not differ significantly with respect to age, gender, or intake symptom severity. Given the similarities across trials, data were pooled for analysis.

Subjects were recruited from UCLA Neuropsychiatric Hospital outpatient clinics and community advertisement. The SCID-I/P and HamD$_{17}$ were used to screen for eligibility; enrolled subjects had HamD$_{17}$ scores≧16 and had no suicidal intent or history of attempt at entry. Exclusion criteria included psychotic symptoms, cluster A or B Axis II disorders, prior suicidal ideation, or any serious medical conditions known to affect brain function or to contraindicate use of the active medication. Subjects were free of psychotropic medications for two weeks prior to enrollment, and psychotropic medications other than the study drug were not permitted for the duration of the trial.

Subjects received one week of single-blinded treatment with placebo prior to eight weeks of randomized double-blinded treatment with medication (fluoxetine 20 mg or venlafaxine 150 mg; n=37) or placebo (n=35). Venlafaxine was dosed as in the normals' study (37.5 mg/day to start with increases to achieve 150 mg after 10 days); fluoxetine dosing was constant at 20 mg/day. Placebo was administered on the same schedule as active drug within each trial to preserve blinding. Clinical symptoms were assessed at: baseline, end of placebo lead-in, and at 48 hours, 1 week, 2 weeks, 4 weeks, and 8 weeks after randomization. Through week 4, the clinical assessment timepoints mirrored those in the 4-week study of healthy subjects; an additional (week 8) assessment was evaluated in the MDD trials.

Adverse mood symptoms were assessed using items from the HamD$_{17}$ and the Symptom Checklist-90-R (SCL-90-R) (Derogatis 1994). We assessed depressed mood using HamD$_{17}$ item #1; suicidal ideation using HamD$_{17}$ item #3; anxiety using the sum of HamD$_{17}$ items #10 and #11 (psychic anxiety and somatic anxiety); and hostility using the SCL-90 hostility subscale (sum of items #11, 24, 63, 67, 74, 81). Subjects were characterized as worseners or non-worseners with respect to each of these adverse mood symptoms.

QEEG Techniques

EEG recordings were performed using the QND system (Neurodata, Inc.; Pasadena, Calif.) while subjects rested in the eyes-closed, maximally alert state in a sound-attenuated room with subdued lighting, using procedures previously described elsewhere in detail (Cook et al 1998, 1999, Leuchter et al 1999). Thirty-five electrodes were positioned with an electrode cap (ElectroCap; Eaton, Ohio) using an extended International 10-20 System. Eye movement was monitored using right infraorbital and left outer canthus electrodes. We collected data using a Pz reference montage and digitized the data at 256 samples/channel/sec, using a high-frequency filter of 70 Hz and a low-frequency filter of 0.3 Hz. Data were reformatted by amplitude subtraction to construct a linked-ears reference and bipolar channel montages. A first technologist reviewed the data for artifacts including eye and muscle movements. A second technologist blinded to subject identity and treatment condition selected the first 20-32 seconds of artifact-free data for processing. This amount of data has been used to obtain reliable frequency spectra (Leuchter et al 1999). Absolute power (the intensity of energy in a frequency band in microvolts squared) was calculated in each of four frequency bands (0.5-4 Hz, 4-8 Hz, 8-12 Hz, and 12-20 Hz) using spectral analysis based upon a fast Fourier transform.

Cordance values were calculated for each electrode in each of the four frequency bands using conventional QEEG absolute and relative power measures as described in greater detail elsewhere (Leuchter et al 1999). First, EEG power values were computed using a re-attributional electrode montage that yields a stronger association between EEG and PET measures than traditional reference strategies (FIG. 1). Next, the absolute and relative power values for each electrode site s in each frequency band f were z-transformed to measure deviation from the mean values for that recording, yielding $A_{norm(s,f)}$ and $R_{norm(s,f)}$ respectively. Finally, the z-scores were summed to yield a cordance value, Z, for each electrode in each frequency band where $Z_{(s,f)}=A_{norm(s,f)}+R_{norm(s,f)}$. We limited our analyses to cordance measures from the theta frequency band (4-8 Hz) because previous work has found that energy in this band is associated most strongly with changes in symptoms of depression (Ulrich et al 1984, 1994, Cook et al 1999).

Growth Modeling

In another example, a first part of a study determined whether a flexible growth mixture modeling application would identify a subgroup of depressed patients that exhibits clinical worsening during an initial eight weeks of antidepressant treatment.

Data were obtained from 94 adults with MDD who participated in one of three placebo-controlled trials. Diagnoses of unipolar depression were established with a structured clinical interview (SCID). The trials consisted of a one-week placebo lead-in, followed by eight weeks of double-blind randomized treatment with active drug (fluoxetine 20 mg or venlafaxine 150 mg) or placebo. HamD$_{17}$ scores were obtained at each of the 11 visits: baseline, end of placebo lead-in, 48 hours after start of randomized treatment, and weekly throughout eight weeks of randomized treatment. We applied a 3-piece random effect growth mixture model (Mplus software, version 4.2) focusing on change in HamD$_{17}$ scores over 11 time-points in separate analyses for subjects randomized to medication versus placebo. The growth mixture model extends conventional growth modeling by allowing for different classes of development characterized by their trajectory shapes. The analysis did not specify a priori trajectory shapes but was exploratory in nature, allowing shapes to be found using a flexible growth model.

Figure 9A:
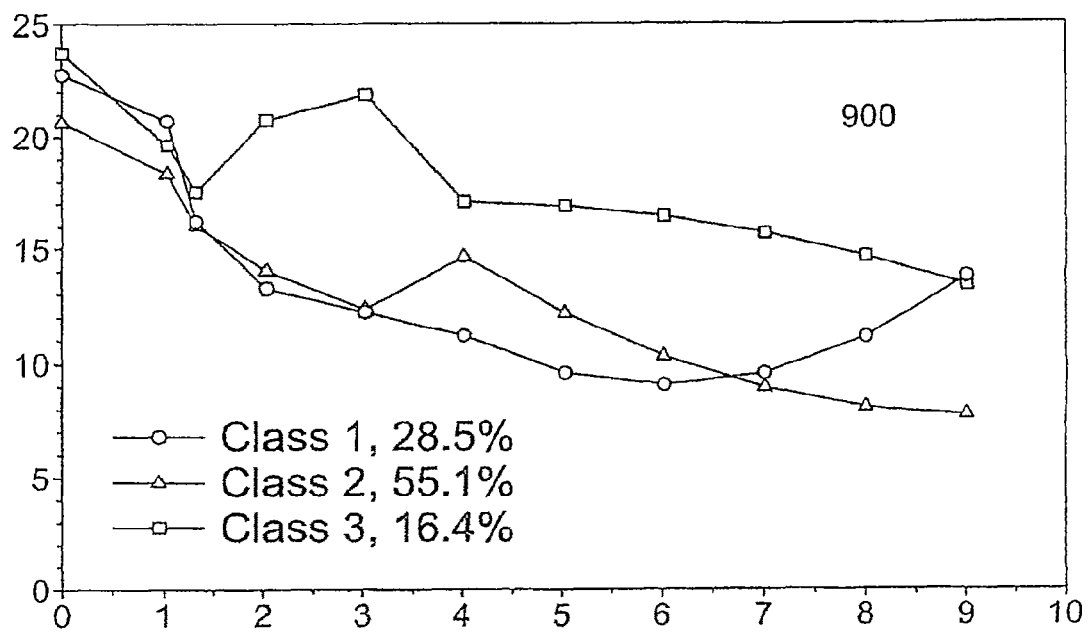
FIG. 9A shows a plot illustrating estimated HamD17 means for three groups of antidepressant-treated subjects (n=49) across time, i.e., over a one week placebo lead-in followed by eight weeks of randomized treatment with antidepressant medication according to an embodiment of the present invention.

FIG. 9A shows a plot 900 illustrating estimated HamD$_{17}$ means for three groups of antidepressant-treated subjects (n=49) across time, i.e., over a one week placebo lead-in followed by eight weeks of randomized treatment with antidepressant medication according to an embodiment of the present invention. Eight of 49 antidepressant-treated subjects (16%) fell into Class 3—showing a clinical trajectory characterized by transient clinical worsening beginning between 48 hours and 1 week after start of medication. In this group, symptoms continued to improve from the placebo lead-in period through the first 48 hours of antidepressant treatment only to increase at weeks 1 and 2—above the level observed at end-of-placebo-lead-in. Subjects is the other two groups, i.e., Classes 1 (n=22; 46%) and 2 (n=17; 41%) did not exhibit any increase>=3 points on the HamD17 at any one-week interval. Importantly, in Classes 1 and 2, symptoms during antidepressant treatment never exceeded the level observed just prior to beginning medication (i.e. end of placebo lead-in). Classes 1 and 2 both showed continued improvement of symptoms after 48 hours on medication through week 6. Class 2 then continued with durable symptom improvement through endpoint, whereas Class 1 exhibited a loss of improvement but without returning to baseline severity at the end of the trial. Whereas estimated means for each class suggest an overall decrease in symptoms from end-of-placebo-lead-in to week 8 for every subgroup, (with Class 2 showing the greatest degree of improvement), the pattern of early symptom changes is markedly different with Class 3 showing abrupt clinical worsening beginning after 48 hours on medication.

Figure 9B:
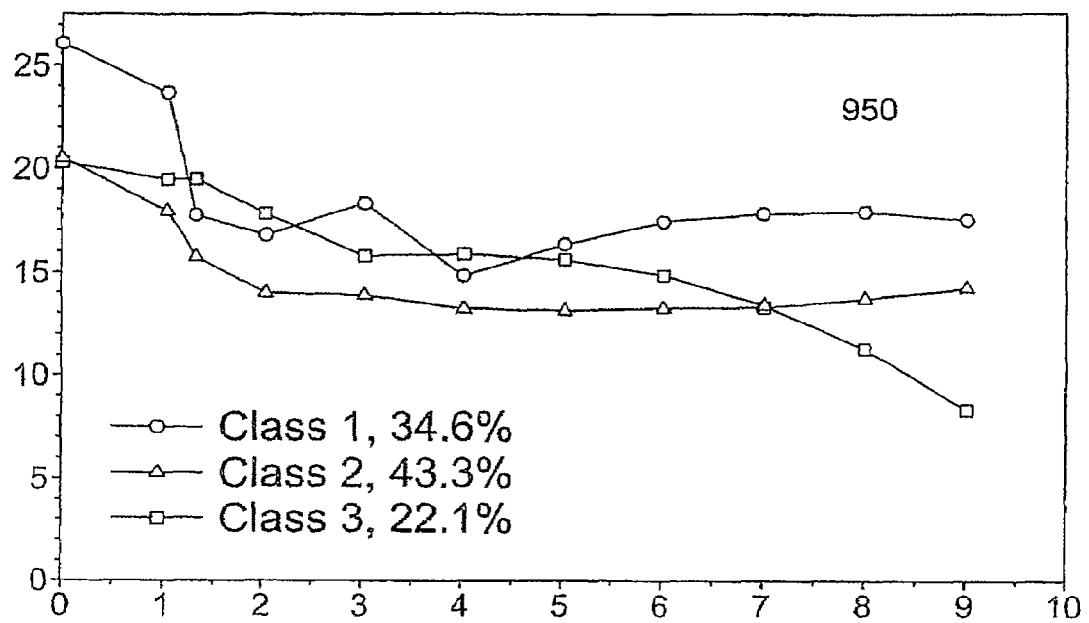
FIG. 9B shows a plot 950 of estimated HamD17 means for three groups of MDD subjects randomized to placebo (total n=45) according to an embodiment of the present invention.

In order to compare symptom trajectories between antidepressant- and placebo-treated subjects, we examined those subjects randomized to placebo (n=45) from the same three placebo-controlled trials. As illustrated in FIG. 8B, application of the same 3-piece random effect growth mixture model in placebo subjects did not reveal a clear worsening group. FIG. 9B shows a plot 950 of estimated HamD17 means for three groups of MDD subjects randomized to placebo (total n=45) according to an embodiment of the present invention.

Embodiments of the present invention used a change in midline-and-light-frontal cordance (i.e., MRFC) 48 hours after start of treatment to predict Class 3 membership in MDD subjects randomized to antidepressant treatment. Based upon EEG data available for 47 of 49 medication subjects from this dataset, binary logistic regression analysis showed that the cordance variable significantly predicted membership in class 3 (volatile class) versus classes 1 and 2 combined (p=0.028, 2-tailed). Table I shows the variables in the regression equation.

TABLE I

Variables in the Equation

| | | B | S.E. | Wald | df | Sig. | Exp(B) |
|---|---|---|---|---|---|---|---|
| Step 1(a) | MRFCW48all Ss | −1.395 | .635 | 4.830 | 1 | .028 | .248 |
| | Constant | −2.079 | .540 | 14.845 | 1 | .000 | .125 |

Figure 10:
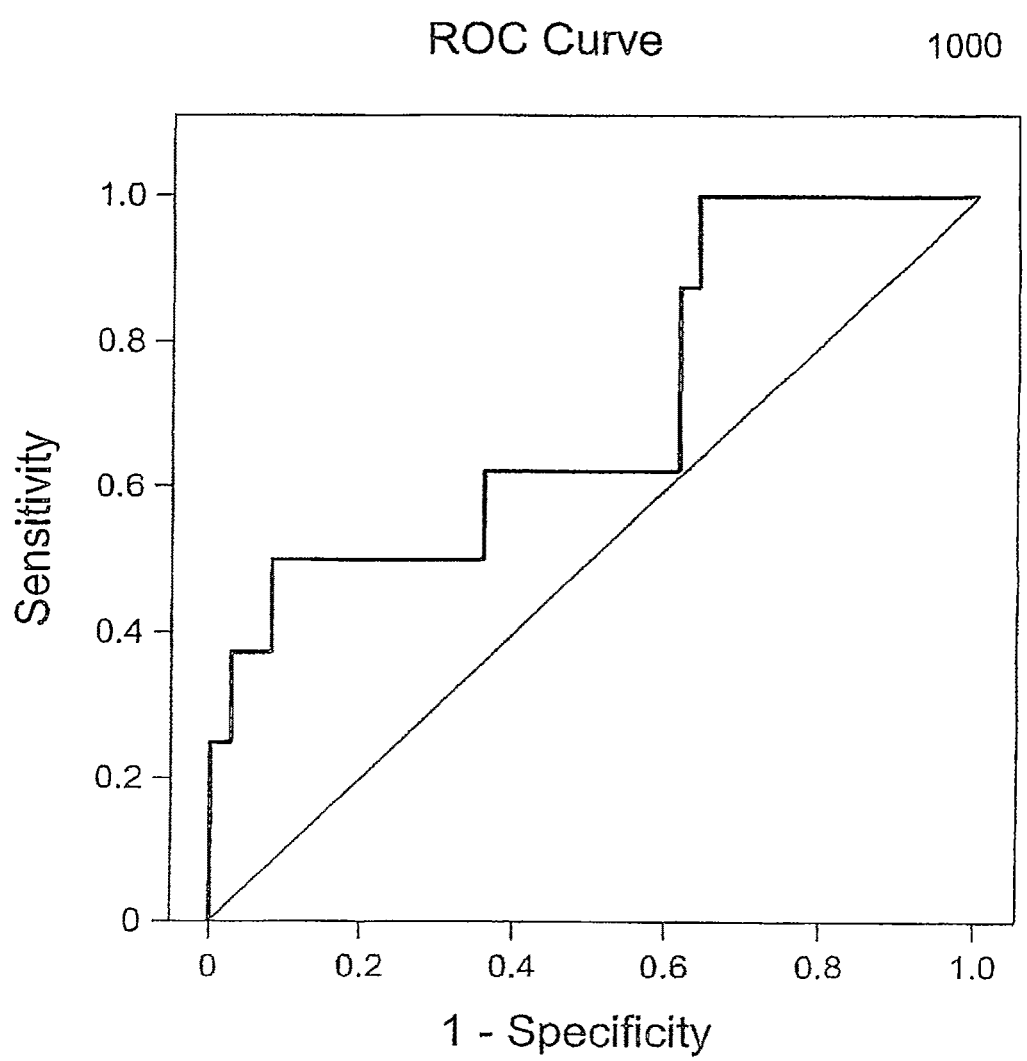
FIG. 10 is a plot 1000 illustrating an ROC curve for the identification of a subgroup of depressed patients that exhibits clinical worsening during an initial eight weeks of antidepressant treatment. The area under the curve is 0.708.

Table II shows a summary of the model from the regression analysis. The estimation terminated at iteration number 5 because parameter estimates changed by less than 0.001. FIG. 10 is a plot 1000 illustrating an ROC curve for the identification of a subgroup of depressed patients that exhibits clinical worsening during an initial eight weeks of antidepressant treatment. The area under the curve is 0.708.

TABLE II

Model Summary

| Step | −2 Log likelihood | Cox & Snell R Square | Nagelkerke R Square |
|---|---|---|---|
| 1 | 36.839(a) | .121 | .202 |

The Growth mixture modeling shows that a small group of antidepressant-treated subjects have a more volatile course of symptom fluctuation as assessed by the pattern of total $HamD_{17}$ score changes over time. Changes in MFRC 48 hours after start of antidepressant medication predicted membership in the group of subjects who had more volatile symptom fluctuation during antidepressant treatment. Receiver Operating Characteristic (ROC) analysis yielded an overall accuracy of 71%.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, along with a processor which can execute instructions on the computer readable medium, and may be present on or within different computational apparatuses within a system or network.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

BIBLIOGRAPHY

Bares M, Brunovsky M, Kopecek M, Stopková P, Novák T, Kozeny J, et al. Changes in QEEG prefrontal activity as a predictor of response to antidepressive medication in patients with treatment resistant depressive disorder: a pilot study. 14th European Congress of Psychiatry, AEP, Mar. 4-8, 2006, Nice, France Brody A L, Saxena S, Stoessel P, Gillies L A, Fairbanks L A, Alborzian S, et al (2001): Regional Brain Metabolic Changes in Patients with Major Depression Treated with Either Paroxetine or Interpersonal Therapy: Preliminary Findings. Arch Gen Psychiatry 58:631-640.

Cook I A, Hunter A M, Abrams M, Siegman B, Leuchter A F. Midline and right frontal brain function and remission in major depression. 2006 Poster presented at the New Clinical Drug Evaluation Unit (NCDEU) Annual Meeting.

Cook I A, Leuchter A F, Morgan M, Witte E, Stubbeman W F, Abrams M, et al (2002): Early Changes in Prefrontal Activity Characterize Clinical Responders to Antidepressants. Neuropsychopharmacology 27(1): 120-131.

Cook I A, Leuchter A F, Morgan M L, Stubbeman W, Siegman B, Abrams M (2005): Changes in Prefrontal Activity Characterize Clinical Response in SSRI Nonresponders: A Pilot Study. J Psychiatr Res 39(5):461-6.

Cook I A, Leuchter A F, Uijtedehaage S H J, Abrams M, Anderson-Hanley C, Rosenberg-Thompson S, Dunkin J (1999): Neurophysiologic Predictors of Treatment Response to Fluoxetine in Major Depression. Psychiatry Res 85:263-273.

Cook I A, Leuchter A F (2001): Prefrontal Changes and Treatment Response Prediction in Depression. Seminars Clin Neuropsychiatry 6:113-20.

Cook I A, O'Hara R, Uijtdehaage S H J, Mandelkern M, Leuchter A F (1998): Assessing the Accuracy of Topographic EEG Mapping for Determining Local Brain Function. Electroencephalogr Clin Neurophysiol 107:408-414.

Derogatis L R (1994): Symptom Checklist-90-R: Administration, Scoring and Procedures Manual, 3rd ed. Minneapolis, Minn.: National Computer Systems.

Drevets W C, Bogers W, Raichle M E (2002): Functional Anatomical Correlates of Antidepressant Drug Treatment Assessed Using PET Measures of Regional Glucose Metabolism. Eur Neuropsychopharmacol 12(6):527-44.

First M B, Spitzer R L, Gibbon M, Williams J B W (1996): Structured Clinical Interview for DSM-IV Axis I Disorders—Patient Edition (SCID-I/P, Version 2.0). New York: Biometrics Research Department, New York State Psychiatric Institute.

Hamilton M (1960): A Rating Scale for Depression. J Neurol Neurosurg Psychiatry 23:56-62.

Hunter A M, Leuchter A F, Morgan M L, Cook I A, DeBrota D J, Potter W Z (2005): Neurophysiologic Correlates of Side Effects in Normal Subjects Randomized to Venlafaxine or Placebo. Neuropsychopharmacology 30:792-799.

Hunter A M, Leuchter A F, Morgan M L, Cook I A (in press): Changes in Brain Function (QEEG Cordance) During Placebo Lead-in and Treatment Outcomes in Clinical Trials for Major Depression. American Journal of Psychiatry.

Iosifescu D V, Greenwald S, Devlin P, Perlis R H, Alpert J E, Hamill S, Sklarsky K G, Fava M. Pretreatment Frontal EEG Predicts Changes in Suicidal Ideation During SSRI Treatment in MDD. Presented at the 45th Annual New Clinical Drug Evaluation Unit (NCDEU) Meeting, 2005a Boca Raton, Fla.

Kopecek M, Bares M, Brunovsky M, Stopková P, Novák T, Kozeny J, et al. EEG cordance as a predictor of response to antidepressive medication—pooled analysis. 14th European Congress of Psychiatry, AEP, Mar. 4-8, 2006, Nice.

Leuchter A F, Cook I A, Uijtdehaage S H, Lufkin R B, Anderson-Hanley C, Abrams M, et al (1997): Brain Structure and Function, and the Outcomes of Treatment for Depression. J Clin Psychiatry 58(Suppl 16):22-31.

Leuchter A F, Cook I A, DeBrota D J, Hunter A M, Potter W Z, McGrouther C C, et al (under review): Changes in Brain Function (QEEG Cordance) During Administration of Venlafaxine or Placebo to Normal Subjects. International Journal of Neuropsychopharmacology.

Leuchter A F, Cook I A, Hunter A M, Morgan M L, McGrouther C C, Abrams M. Functional brain changes associated with remission in major depressive disorder. Poster presented at the Society of Biological Psychiatry Meeting; 2005; Atlanta, Ga.

Leuchter A F, Cook I A, Witte E A, Morgan M, Abrams M (2002): Changes in Brain Function of Depressed Subjects During Treatment with Placebo. Am J Psychiatry 159(1): 122-9.

Leuchter A F, Uijtdehaage S H, Cook I A, O'Hara R, Mandelkern M (1999): Relationship Between Brain Electrical Activity and Cortical Perfusion in Normal Subjects. Psychiatry Res 90:125-40.

Mayberg H S (2003): Modulating Dysfunctional Limbic-cortical Circuits in Depression: Towards Development of Brain-based Algorithms for Diagnosis and Optimised Treatment. Br Med Bull 65:193-207.

Mayberg H S, Brannan S K, Mahurin R K, Jerabek P A, Brickman J S, Tekell J L, et al (1997): Cingulate Function in Depression: A Potential Predictor of Treatment Response. Neuroreport 8(15):i-ii.

Mayberg H S, Brannan S K, Tekell J L, Silva J A, Mahurin R K, McGinnis S, Jerabek P A (2000): Regional Metabolic Effects of Fluoxetine in Major Depression: Serial Changes and Relationship to Clinical Response. Biol Psychiatry 48(8):830-43.

Ulrich G, Haug H J, Fahndrich E (1994): Acute Versus Chronic EEG Effects of Maprotiline- and in Clomipramine-treated Depressive Inpatients and the Prediction of Therapeutic Outcome. J Affect Disord 32:213-217.

Ulrich G, Renfordt E, Zeller G, Frick K (1984): Interrelation Between Changes in the EEG and Psychopathology Under Pharmacotherapy for Endogenous Depression. A Contribution to the Predictor Question. Pharmacopsychiatry (6): 178-83.

What is claimed is:

1. A method of identifying subjects at risk for an adverse effect from treatment with a serotonin reuptake inhibitor, the method comprising:
at a computer system comprising a processor, memory, and at least one program stored in the memory and executable by the processor:
receiving a first set of physical values that are obtained by measuring one or more physical properties of a subject's brain activity at a first time, wherein the first time is before the subject begins treatment with the serotonin reuptake inhibitor;
calculating a first resultant value of a function using the first set of physical values as input values, wherein the function is midline and right frontal cordance (MRFC);
receiving a second set of physical values that are obtained by measuring one or more physical properties of a subject's brain activity at a second time, wherein the second time is after the subject begins treatment with the serotonin reuptake inhibitor;
calculating a second resultant value of the function using the second set of physical values as input values;
determining a change in the function from the first time to the second time by calculating a difference value between the first and second resultant values; and
based on the difference value, determining whether the subject is at risk for a future adverse effect from treatment with the serotonin reuptake inhibitor, wherein the subject's brain activity is measured using an electroencephalograph.

2. The method of claim 1, wherein the subject's brain activity is measured using electroencephalography.

3. The method of claim 2, wherein the one or more physical properties of the subject's brain activity comprise voltages measured at electrodes fp2, af2, f4, f8, fz, and fpz, placed according to the extended international 10-20 system.

4. The method of claim 3, wherein the one or more physical properties of the subject's brain activity consist of voltages measured at electrodes fp2, af2, f4, f8, fz, and fpz, placed according to the extended international 10-20 system.

5. The method of claim 1, wherein the second time is less than or equal to about 48 hours after treatment begins with the serotonin reuptake inhibitor.

6. The method of claim 1, wherein the physical properties of the brain activity consist of theta waves.

7. The method of claim 1, wherein the adverse effect comprises at least one of depressed mood, anxiety, hostility, and suicidal ideation.

8. The method of claim 1, wherein determining whether the subject is at risk for a future adverse effect from treatment with the serotonin reuptake inhibitor includes determining a percentage or range of percentages for a likelihood of a future adverse effect.

9. The method of claim 1, wherein determining whether the subject is at risk for a future adverse effect from treatment with the serotonin reuptake inhibitor includes comparing the difference value to a cutoff value.

10. The method of claim 9, wherein the cutoff value is determined by:
acquiring data of mood and brain activity properties at a plurality of different times from a plurality of subjects, wherein at least one time is before treatment and one time is after treatment with the serotonin reuptake inhibitor;
determining optimal physical properties by pattern classification;

examining changes in values of the physical properties among the different times;

assessing an association between changes in mood data and optimal physical properties; and determining a cut off value when an association is identified.

11. The method of claim 1, wherein the serotonin reuptake inhibitor is a selective serotonin reuptake inhibitor.

12. The method of claim 1, wherein the serotonin reuptake inhibitor also inhibits norepinephrine reuptake.

13. The method of claim 1, wherein the serotonin reuptake inhibitor is fluoxetine or venlafaxine.

14. A non-transitory computer readable storage medium storing one or more programs for identifying subjects at risk for an adverse effect from treatment with a serotonin reuptake inhibitor comprising instructions for execution by a processor, which when executed by a computer system with one or more processors, cause the computer system to:

(A) receive a first set of physical values that are obtained by measuring one or more physical properties of a subject's brain activity at a first time, wherein the first time is before the subject begins treatment with the serotonin reuptake inhibitor;

(B) calculate a first resultant value of a function using the first set of physical values as input values, wherein the function is midline and right frontal cordance (MRFC);

(C) receive a second set of physical values that are obtained by measuring one or more physical properties of a subject's brain activity at a second time, wherein the second time is after the subject begins treatment with the serotonin reuptake inhibitor;

(D) calculate a second resultant value of the function using the second set of physical values as input values;

(E) determine a change in the function from the first time to the second time by calculating a difference value between the first and second resultant values; and (E) based on the comparison, determine whether the subject is at risk for a future adverse effect from treatment with the serotonin reuptake inhibitor.

15. The non-transitory computer readable storage medium of claim 14, wherein the subject's brain activity is measured using electroencephalography.

16. The non-transitory computer readable storage medium of claim 15, wherein the one or more physical properties of the subject's brain activity comprise voltages measured at electrodes fp2, af2, f4, f8, fz, and fpz, placed according to the extended international 10-20 system.

17. The non-transitory computer readable storage medium of claim 16, wherein the one or more physical properties of the subject's brain activity consist of voltages measured at electrodes fp2, af2, f4, f8, fz, and fpz, placed according to the extended international 10-20 system.

18. The non-transitory computer readable storage medium of claim 14, wherein the second time is less than or equal to about 48 hours after treatment begins with the serotonin reuptake inhibitor.

19. The non-transitory computer readable storage medium of claim 14, wherein the physical properties of the brain activity consist of theta waves.

20. The non-transitory computer readable storage medium of claim 14, wherein determining whether the subject is at risk for a future adverse effect from treatment with the serotonin reuptake inhibitor includes determining a percentage or range of percentages for a likelihood of a future adverse effect.

21. The non-transitory computer readable storage medium of claim 14, wherein determining whether the subject is at risk for a future adverse effect from treatment with the serotonin reuptake inhibitor includes comparing the difference value to a cutoff value.

22. The non-transitory computer readable storage medium of claim 21, wherein the cutoff value is determined by:

acquiring data of mood and brain activity properties at a plurality of different times from a plurality of subjects, wherein at least one time is before treatment with the serotonin reuptake inhibitor and one time is after treatment with the serotonin reuptake inhibitor;

determining optimal physical properties by pattern classification;

examining changes in values of the physical properties among the different times;

assessing an association between changes in mood data and optimal physical properties; and determining a cut off value when an association is identified.

23. The non-transitory computer readable storage medium storing one or more programs of claim 14, wherein the serotonin reuptake inhibitor is a selective serotonin reuptake inhibitor.

24. The non-transitory computer readable storage medium storing one or more programs of claim 14, wherein the serotonin reuptake inhibitor also inhibits norepinephrine reuptake.

25. The non-transitory computer readable storage medium storing one or more programs of claim 14, wherein the serotonin reuptake inhibitor is fluoxetine or venlafaxine.

26. A system for predicting adverse antidepressant effects, the system comprising:

a computing system, the computer system comprising:

a processor;

memory; and at least one program stored in the memory and executable by the processor, the program comprising instructions for:

(A) receiving a first set of physical values that are obtained by measuring one or more physical properties of the subject's brain using a plurality of sensors at a first time, wherein the first time is before the subject begins treatment with the serotonin reuptake inhibitor;

(B) calculating a first resultant value of a function using the first set of physical values as input values, wherein the function is midline and right frontal cordance (MRFC);

(C) receiving a second set of physical values that are obtained by measuring one or more physical properties of the subject's brain using the plurality of sensors at a second time, wherein the second time is after the subject begins treatment with the serotonin reuptake inhibitor;

(D) calculating a second resultant value of the function using the second set of physical values as input values;

(E) determining a change in the function from the first time to the second time by calculating a difference value between the first and second resultant values; and (F) based on the comparison, determining whether the subject is at risk for a future adverse effect from treatment with the serotonin reuptake inhibitor.

27. The system of claim 26, wherein the physical properties of the brain activity consist of theta waves.

28. The system of claim 26, wherein the plurality of sensors is a plurality of electrodes configured to measure electromagnetic signals on the subject's head.

29. The system of claim 28, wherein the one or more physical properties of the subject's brain activity comprise voltages measured at electrodes fp2, af2, f4, f8, fz, and fpz, placed according to the extended international 10-20 system, wherein the electrodes are respective electrodes in the plurality of electrodes.

30. The system of claim 29, wherein the one or more physical properties of the subject's brain activity consist of voltages measured at electrodes fp2, af2, f4, f8, fz, and fpz, placed according to the extended international 10-20 system, wherein the electrodes are respective electrodes in the plurality of electrodes.

31. The system of claim 26, wherein determining whether the subject is at risk for a future adverse effect from treatment with the serotonin reuptake inhibitor includes determining a percentage or range of percentages for a likelihood of a future adverse effect.

32. The system of claim 26, wherein determining whether the subject is at risk for a future adverse effect from treatment with the serotonin reuptake inhibitor includes comparing the difference value to a cutoff value.

33. The system of claim 32, wherein the cutoff value is determined by:
   acquiring data of mood and brain activity properties at a plurality of different times from a plurality of subjects, wherein at least one time is before treatment with the serotonin reuptake inhibitor and one time is after treatment with the serotonin reuptake inhibitor;
   determining optimal physical properties by pattern classification;
   examining changes in values of the physical properties among the different times;
   assessing an association between changes in mood data and optimal physical properties; and
   determining a cut off value when an association is identified.

34. The system of claim 26, wherein the serotonin reuptake inhibitor is a selective serotonin reuptake inhibitor.

35. The system of claim 26, wherein the serotonin reuptake inhibitor also inhibits norepinephrine reuptake.

36. The system of claim 26, wherein the serotonin reuptake inhibitor is fluoxetine or venlafaxine.

37. A method for determining the safety of a candidate antidepressant, the method comprising:
   at a computer system comprising a processor, memory, and at least one program stored in the memory and executable by the processor:
   receiving a plurality of first sets of physical values, each respective first set of physical values in the plurality of first sets of physical values obtained by measuring one or more physical properties of a subject's brain activity at a first time, wherein the first time is before the subject begins treatment with the serotonin reuptake inhibitor;
   calculating a plurality of first resultant values of a function, each respective first resultant value in the plurality of first resultant values calculated using the corresponding first set of physical values as input values, wherein the function is midline and right frontal cordance (MRFC);
   receiving a plurality of second sets of physical values, each respective second set of physical values in the plurality of second sets of physical values obtained by measuring one or more physical properties of the subject's brain activity at a second time, wherein the second time is after the subject begins treatment with the serotonin reuptake inhibitor;
   calculating a plurality of second resultant values of the function, each respective second resultant value in the plurality of resultant second values calculated using the corresponding second set of physical values as input values;
   determining a plurality of changes in the function from the first time to the second time, each respective change in the function in the plurality of changes in the function determined by calculating a difference value between the corresponding first and corresponding second resultant values; and
   based on the plurality of difference values, determining whether the candidate antidepressant is likely to pose safety concerns, wherein brain activity is measured using an electroencephalograph.

* * * * *